(12) United States Patent
Gueckel

(10) Patent No.: US 7,977,274 B2
(45) Date of Patent: Jul. 12, 2011

(54) CATALYST WITH BIMODAL PORE SIZE DISTRIBUTION AND THE USE THEREOF

(75) Inventor: Christian Gueckel, Paramus, NJ (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 976 days.

(21) Appl. No.: 11/540,983

(22) Filed: Sep. 29, 2006

(65) Prior Publication Data

US 2008/0081920 A1    Apr. 3, 2008

(51) Int. Cl.
| | |
|---|---|
| B01J 21/00 | (2006.01) |
| B01J 23/50 | (2006.01) |
| B01J 23/00 | (2006.01) |
| B01J 20/00 | (2006.01) |

(52) U.S. Cl. ............. 502/243; 502/64; 502/68; 502/72; 502/80; 502/87; 502/241; 502/263; 502/341; 502/347; 502/348; 502/349; 502/350; 502/351; 502/415; 502/439

(58) Field of Classification Search .......... 502/64, 502/68, 72, 80, 87, 241, 243, 263, 341, 347, 502/348, 349, 350, 351, 415, 439
See application file for complete search history.

(56) References Cited

U.S. PATENT DOCUMENTS

| | | | |
|---|---|---|---|
| 3,563,914 A | | 2/1971 | Wattimena et al. |
| 3,692,698 A | * | 9/1972 | Riley et al. .................... 502/220 |
| 3,702,259 A | | 11/1972 | Nielsen et al. |
| 3,962,136 A | | 6/1976 | Nielsen et al. ................ 252/454 |
| 4,007,135 A | * | 2/1977 | Hayden et al. ................ 502/317 |
| 4,010,115 A | | 3/1977 | Nielsen et al. ................ 252/454 |
| 4,010,155 A | | 3/1977 | Inouye et al. ................. 260/243 |
| 4,012,425 A | | 3/1977 | Nielsen et al. ............. 260/348.5 |

(Continued)

FOREIGN PATENT DOCUMENTS

CA    2 432 200    7/2002

(Continued)

OTHER PUBLICATIONS

International Search Report and Written Opinion dated Aug. 13, 2010.

(Continued)

Primary Examiner — Cam N Nguyen
(74) Attorney, Agent, or Firm — Scully, Scott, Murphy & Presser, P.C.

(57) ABSTRACT

The invention pertains to a catalyst useful for the epoxidation of an olefin. More particularly, the invention pertains to an improved catalyst useful for the epoxidation of ethylene to ethylene oxide. The catalyst has improved selectivity in the epoxidation process. The catalyst comprises a solid support having a surface, which has a first mode of pores which have a diameter ranging from about 0.01 μm to about 5 μm and having a differential pore volume peak in the range of from about 0.01 μm to about 5 μm. The surface then has a second mode of pores, different from the first mode of pores, which second mode of pores have a diameter ranging from about 1 μm to about 20 μm and have a differential pore volume peak in the range of from about 1 μm to about 20 μm. On the bimodal pore surface is a catalytically effective amount of silver or a silver-containing compound, a promoting amount of rhenium or a rhenium-containing compound, and a promoting amount of one or more alkali metals or alkali-metal-containing compounds.

17 Claims, 1 Drawing Sheet

U.S. PATENT DOCUMENTS

| | | | |
|---|---|---|---|
| 4,039,561 A | 8/1977 | Mitsuhata et al. | 260/348.34 |
| 4,066,575 A | 1/1978 | Winnick | 252/475 |
| 4,123,385 A | 10/1978 | Rebsdat et al. | 252/414 |
| 4,168,247 A * | 9/1979 | Hayden et al. | 502/347 |
| 4,242,235 A | 12/1980 | Cognion et al. | |
| 4,301,037 A * | 11/1981 | Sanchez et al. | 502/303 |
| 4,350,616 A | 9/1982 | Boussert | 252/463 |
| 4,740,493 A * | 4/1988 | Boehning et al. | 502/348 |
| 4,761,394 A | 8/1988 | Lauritzen | 502/348 |
| 4,766,105 A | 8/1988 | Lauritzen | 402/216 |
| 4,808,738 A | 2/1989 | Lauritzen | 549/536 |
| 4,820,675 A | 4/1989 | Lauritzen | 502/216 |
| 4,829,043 A * | 5/1989 | Boehning et al. | 502/348 |
| 4,833,261 A | 5/1989 | Lauritzen | 549/536 |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,187,140 A | 2/1993 | Thorsteinson et al. | |
| 5,387,751 A * | 2/1995 | Hayden et al. | 549/534 |
| 5,407,888 A | 4/1995 | Herzog et al. | |
| 5,504,052 A | 4/1996 | Rizkalla et al. | |
| 5,504,053 A * | 4/1996 | Chou et al. | 502/348 |
| 5,507,956 A * | 4/1996 | Bonse et al. | 210/757 |
| 5,518,979 A * | 5/1996 | Bonse et al. | 502/348 |
| 5,703,001 A * | 12/1997 | Rizkalla | 502/347 |
| 5,733,842 A * | 3/1998 | Gerdes et al. | 502/439 |
| 5,750,461 A * | 5/1998 | Engelhardt et al. | 502/347 |
| 5,773,657 A * | 6/1998 | Rutter et al. | 564/450 |
| 5,801,259 A * | 9/1998 | Kowaleski | 549/536 |
| 5,935,897 A * | 8/1999 | Trubenbach et al. | 502/172 |
| 5,935,898 A * | 8/1999 | Trubenbach et al. | 502/300 |
| 6,245,698 B1 | 6/2001 | Pope et al. | 501/12 |
| 6,299,995 B1 * | 10/2001 | Abdo et al. | 429/17 |
| 6,571,214 B2 | 5/2003 | Newman et al. | |
| 6,573,214 B2 * | 6/2003 | Abdo et al. | 502/332 |
| 6,670,303 B1 | 12/2003 | Heineke et al. | 502/349 |
| 6,831,037 B2 * | 12/2004 | Szymanski et al. | 502/355 |
| 6,984,310 B2 * | 1/2006 | Ginestra et al. | 208/137 |
| 7,102,022 B2 | 9/2006 | Evans et al. | |
| 7,186,757 B2 * | 3/2007 | Espinoza et al. | 518/715 |
| 7,247,600 B2 * | 7/2007 | Lockemeyer | 502/347 |
| 7,259,129 B2 * | 8/2007 | Matusz et al. | 502/347 |
| 7,348,444 B2 | 3/2008 | Evans et al. | |
| 7,388,119 B2 | 6/2008 | Bottcher et al. | |
| 7,449,496 B2 * | 11/2008 | Jin et al. | 518/700 |
| 7,479,565 B2 | 1/2009 | Yeates et al. | |
| 7,507,844 B2 * | 3/2009 | Pak | 549/534 |
| 7,538,235 B2 * | 5/2009 | Lockemeyer | 549/534 |
| 7,547,795 B2 * | 6/2009 | Matusz et al. | 549/512 |
| 7,553,795 B2 * | 6/2009 | Bortinger et al. | 502/347 |
| 7,615,654 B2 * | 11/2009 | Le-Khac et al. | 549/513 |
| 7,671,222 B2 * | 3/2010 | Kaminsky et al. | 549/533 |
| 2002/0004452 A1 * | 1/2002 | Abdo et al. | 502/332 |
| 2002/0091291 A1 * | 7/2002 | Nakashiro | 568/956 |
| 2003/0144141 A1 * | 7/2003 | Bowman et al. | 502/302 |
| 2004/0170556 A1 * | 9/2004 | Szymanski et al. | 423/628 |
| 2004/0198992 A1 * | 10/2004 | Matusz et al. | 549/533 |
| 2004/0260103 A1 * | 12/2004 | Matusz et al. | 549/534 |
| 2005/0096219 A1 * | 5/2005 | Szymanski et al. | 502/439 |
| 2005/0107479 A1 * | 5/2005 | Espinoza et al. | 518/718 |
| 2007/0111886 A1 * | 5/2007 | Serafin et al. | 502/348 |
| 2007/0149792 A1 * | 6/2007 | Zhang et al. | 549/536 |
| 2007/0184973 A1 | 8/2007 | Lockemeyer et al. | |
| 2008/0015393 A1 | 1/2008 | Matusz et al. | |
| 2008/0081920 A1 | 4/2008 | Guekcel | |
| 2008/0125610 A1 | 5/2008 | Lockemeyer et al. | |

FOREIGN PATENT DOCUMENTS

| | | |
|---|---|---|
| EP | 0352850 A1 | 1/1990 |
| EP | 0480538 | 4/1992 |
| EP | 0501317 | 9/1992 |
| EP | 1074301 B1 | 2/2001 |
| EP | 1458698 B1 | 4/2005 |
| WO | WO02/051547 | 7/2002 |
| WO | WO2004078737 A1 | 9/2004 |
| WO | 2006133183 | 12/2006 |
| WO | 2006133187 | 12/2006 |

OTHER PUBLICATIONS

Request for Inter Partes Re-examination for U.S. Appl. No. 7,507,845 issued in a related U.S. Patent Application, namely U.S. Serial No. 95/001,445, together with its attachments.

Re-Examination Non-Final Office Action dated Dec. 7, 2010 in a related U.S. Patent Application, namely U.S. Serial No. 95/001,445.

Office Action received in a related U.S. Patent Application, namely U.S. Appl. No. 12/360,482.

Horvath, I. T., "Encyclopedia of Catalysis, Epoxidation—Industrial" ("Encyclopedia of Catalysis"), 2003, vol. 3, pp. 246-264, Wiley-Interscience.

Third Party Requester's Comments to Patent Owners Reply of Feb. 7, 2011 Pursuant to 37 C.F.R. § 1.947 for U. S. Patent 7,507,845 together with attachments.

* cited by examiner

CATALYST WITH BIMODAL PORE SIZE DISTRIBUTION AND THE USE THEREOF

BACKGROUND OF THE INVENTION

1. Field of the Invention

The invention pertains to a catalyst useful for the epoxidation of an olefin to an olefin oxide. More particularly, the invention pertains to an improved catalyst useful for the epoxidation of ethylene to ethylene oxide. The catalyst has improved selectivity in the epoxidation process.

2. Description of the Related Art

There is continuing interest in producing improved catalysts for the epoxidation of olefins. Of particular interest are catalysts for the highly selective epoxidation of ethylene. These catalysts typically comprise a porous refractory support such as alpha alumina, which has on its surface a catalytic amount of silver and at least one promoter that helps to increase selectivity in the epoxidation process. The use of alkali metals and transition metals as promoters for silver catalysts is well known for the production of ethylene oxide by the partial oxidation of ethylene in the vapor phase. Examples of catalysts are disclosed in U.S. Pat. Nos. 4,010,155; 4,012,425; 4,123,385; 4,066,575; 4,039,561 and 4,350,616. Such highly selective catalysts contain, in addition to silver, selectivity-enhancing promoters such as rhenium, molybdenum, tungsten or nitrate- or nitrite-forming compounds, as discussed in U.S. Pat. Nos. 4,761,394 and 4,766,105. The catalyst may comprise further elements like alkali metals as described in U.S. Pat. No. 3,962,136 and U.S. Pat. No. 4,010,115.

Over the last two decades, rhenium was described as being effective in improving the selectivity of alkaline metal promoted silver-based catalyst supported by a refractory porous support. Some references in the art are U.S. Pat. Nos. 4,761,394 and 4,833,261. The further improvement of silver-based catalyst promoted with alkaline metals and rhenium by the use of sulfur, Mo, W, Cr was disclosed in U.S. Pat. Nos. 4,766,105; 4,820,675 and 4,808,738. EP 1 074 301 B1 and WO 2002/051547 disclose a catalyst containing aluminum oxide, titanium oxide and/or silicon oxide and at least one element of the first and second main group, an element of the third sub-group and an element of the eighth sub-group with bimodal pore size distribution for the dehydrogenation of $C_2$-$C_{16}$ hydrocarbons.

Beside the chemical composition of a supported silver-based epoxidation catalyst, the physical characteristics of the finished catalyst as well the support have been an integral part of catalyst development. Generally, the silver-based catalyst support shows a characteristic pore volume and pore size distribution. Furthermore, the surface area and the water absorption are well-known characteristics for such catalyst supports. It has now been found that the physical characteristics of the finished catalyst and the impact of the characteristics on the catalyst performance are more complicated than heretofore believed, especially if the catalyst is promoted with rhenium. In addition to the surface area, the pore volume and the pore size distribution, the pattern of the pore size distribution, especially the number and the specific characteristics of different modes, has now been found to have a significant positive impact on the catalyst selectivity.

It has been unexpectedly found that improved catalysts selectivity can be attained when the silver, rhenium and promoters are deposited onto a solid support having a bimodal pore distribution.

SUMMARY OF THE INVENTION

The invention provides a catalyst for the epoxidation of an olefin to an olefin oxide comprises a support having a bimodal pore size distribution, with a first mode of pores which has a mean diameter ranging from about 0.01 μm to about 5 μm, and a second mode of pores which has a mean diameter ranging from about 5 μm to about 30 μm; a catalytically effective amount of silver or a silver-containing compound, a promoting amount of rhenium or a rhenium-containing compound, and a promoting amount of one or more alkali metals or alkali-metal-containing compounds.

The invention also provides process for the oxidation of an olefin to an olefin oxide which comprises the vapor phase oxidation of an olefin with molecular oxygen in a fixed bed, tubular reactor, in the presence of the catalyst.

The invention also provides process for the oxidation of ethylene to ethylene oxide which comprises the vapor phase oxidation of ethylene with molecular oxygen in a fixed bed, tubular reactor, in the presence of the catalyst.

DETAILED DESCRIPTION OF THE INVENTION

Figure 1:
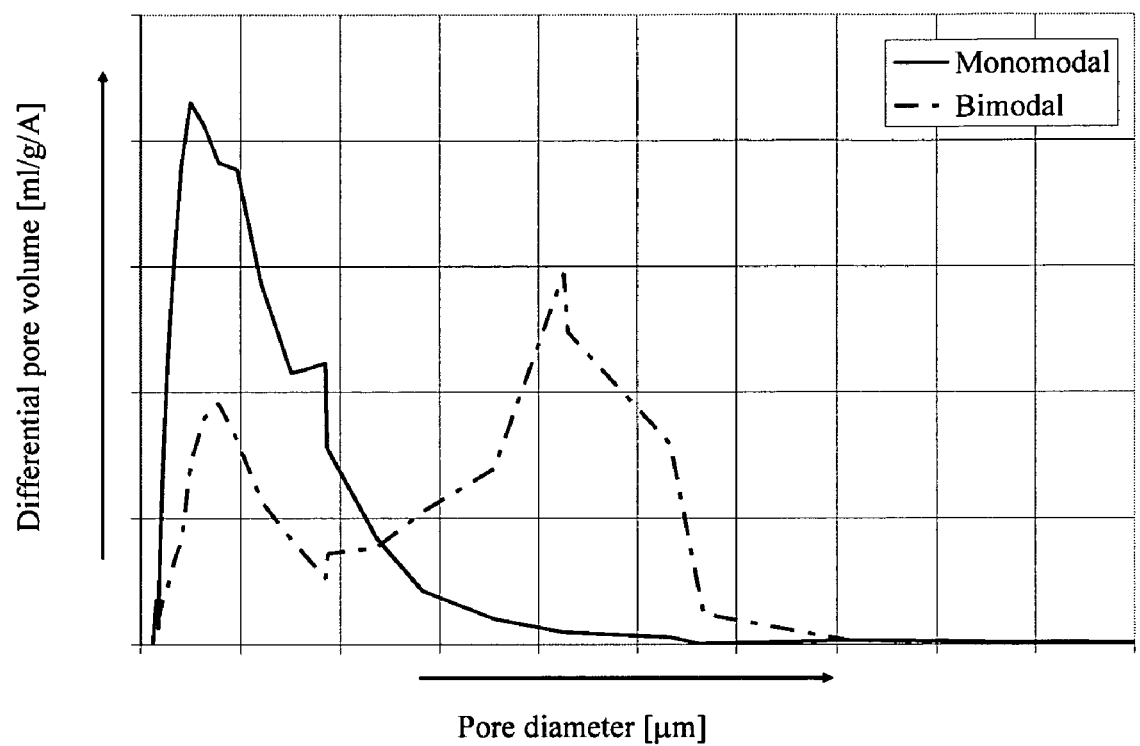
FIG. 1 shows a graph of a monomodal vs. a bimodal pore size distribution.

The support employed in this invention may be selected from a large number of solid, refractory supports that are porous and provide the preferred pore structure. Alumina is well known to be useful as a catalyst support for the epoxidation of an olefin and is the preferred support. The alumina support may also contain various impurities and additives which may or may not influence the catalytic epoxidation reaction. In the process of making the preferred alumina support, high-purity aluminum oxide, preferably alpha-alumina, is thoroughly mixed with temporary and permanent binders. The temporary binders, known as burnout materials, are thermally decomposable organic compounds of moderate to high molecular weight which, on decomposition, alter the pore structure of the support. The permanent binders are typically inorganic clay-type materials having fusion temperatures below that of the alumina and impart mechanical strength to the finished support. After thorough dry-mixing, sufficient water and/or other suitable liquid is added to help form the mass into a paste-like substance. Catalyst support particles are then formed from the paste by conventional means such as extrusion. The particles are then dried and are subsequently calcined at an elevated temperature.

The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. The preferred support is comprised of alpha-alumina having a very high purity; i.e., at least 95 wt. % pure, or more preferably, at least 98 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

According to the invention, the solid support surface has a first mode of pores which have a mean diameter ranging from about 0.01 μm to about 5 μm. Preferably the first mode of pores has a mean diameter ranging from about 0.1 μm to about 4 μm. The surface then has a second mode of pores, different from the first mode of pores, which second mode of pores has a mean diameter ranging from about 5 μm to about 30 μm. Preferably the second mode of pores has a mean diameter ranging from about 5 μm to about 20. Usually, the first mode of pores comprises from about at most about 50% of the total pore volume and the second mode provides at least about 50% of the total pore volume. In another embodiment, the first mode of pores comprises at most about 45% of the total pore volume and the second mode provides at least about 55% of the total pore volume. In another embodiment, the first mode of pores comprises at most about 40% of the total pore volume and the second mode provides at least about 60% of the total pore volume. It is believed, without limiting the scope of the invention that a catalyst with the described bimodal pore size distribution provides advantageous pore structure with reaction chambers separated by diffusion channels. The surface acidity of the support, as determined by irreversible ammonia sorption at 100° C., is often less than about 2 micromoles per gram of support, preferably less than about 1.5 micromoles per gram of support, and often from about 0.05 to 1.0 about micromoles per gram of support. FIG. 1 shows a graph of a monomodal vs. a bimodal pore size distribution.

The final support usually has a water absorption values ranging from about 0.2 cc/g to about 0.8 cc/g, preferably from about 0.25 cc/g to about 0.6 cc/g. The BET surface area of the finished alumina and/or mixed metal oxide is preferred to be in the range of 0.4-4.0 m$^2$/g, more preferably from about 0.5 to about 1.5 m$^2$/g, and most preferably from about 0.5 m$^2$/g to about 1 m$^2$/g. Preferably the support comprises alumina with a surface area of less than about 1 m$^2$/g. Suitable porosity volumes measured by mercury intrusion techniques are expected to be in the range of from about 0.2 ml/g to about 0.8 ml/g, preferably from about 0.25 ml/g to about 0.60 ml/g.

Regardless of the character of the support used, it is usually shaped into particles, chunks, pieces, pellets, rings, spheres, wagon wheels, cross-partitioned hollow cylinders, and the like, of a size suitable for employment in fixed-bed epoxidation reactors. Desirably, the support particles may have equivalent diameters in the range of from about 3 mm to about 12 mm and preferably in the range of from about 5 mm to about 10 mm, which are usually compatible with the internal diameter of the tubular reactors in which the catalyst is placed. Equivalent diameter is the diameter of a sphere having the same external surface (i.e. neglecting surface within the pores of the particle) to volume ratio as the support particles being employed.

In general, a suitable catalyst support of the present invention can be prepared by mixing the refractory material, such as alumina, water or other suitable liquid, a burnout material or suitable porosity-controlling agent, and a binder. Burnout materials include cellulose, substituted celluloses, e.g. methylcellulose, ethylcellulose, and carboxyethylcellulose, stearates, such as organic stearate esters, e.g. methyl or ethyl stearate, waxes, granulated polyolefins, particularly polyethylene and polypropylene, walnut shell flour, and the like which are decomposable at the firing temperatures used in preparation of the support. The burnout is used to modify the porosity of the support. It is essentially totally removed during the firing to produce the finished support. Supports of the present invention are preferably made with the inclusion of a bonding material such as silica with an alkali metal compound in sufficient amount to substantially prevent the formation of crystalline silica compounds. Appropriate binders include inorganic clay-type materials. A particularly convenient binder material is a mixture of boehmite, an ammonia stabilized silica sol, and a soluble sodium salt.

A paste is formed by mixing the dry ingredients of the support with water or other suitable liquid, and the paste is usually extruded or molded into the desired shape, and then fired or calcined at a temperature of from about 1200° C. to about 1600° C. to form the support. When the particles are formed by extrusion, it may be desirable to also include extrusion aids. The amounts of extrusion aids required would depend on a number of factors that relate to the equipment used. However these matters are well within the general knowledge of a person skilled in the art of extruding ceramic materials. After firing, the support is preferably washed to remove soluble residues. Washing is most commonly done with water but washing with other solvents or aqueous/non-aqueous solutions can also be beneficial. Suitable supports having a bimodal pre distribution are available from Saint-Gobain Norpro Co., Noritake Co., and Sued Chemie AG, CeramTec AG.

In order to produce a catalyst for the oxidation of ethylene to ethylene oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used. After impregnation, the excess solution is removed from the impregnated support, and the impregnated support is heated to evaporate the solvent and to deposit the silver or silver compound on the support as is known in the art.

Preferred catalysts prepared in accordance with this invention contain up to about 45% by weight of silver, expressed as metal, based on the total weight of the catalyst including the support. The silver is deposited upon the surface and throughout the pores of a porous refractory support. Silver contents, expressed as metal, of from about 1% to about 40% based on the total weight of the catalyst are preferred, while silver contents of from about 8% to about 35% are more preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Useful silver containing compounds which are silver precursors non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

Also deposited on the support, either prior to, coincidentally with, or subsequent to the deposition of the silver is a promoting amount of a rhenium component, which may be a rhenium-containing compound or a rhenium-containing complex. The rhenium promoter may be present in an amount of from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Also deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of silver, support, alkali metal promoters, rhenium component, and optional additional promoters of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity. In the epoxidation process, it may be desirable to intentionally change the operating conditions to take advantage of certain catalytic properties even at the expense of other catalytic properties. The preferred operating conditions will depend upon, among other factors, feedstock costs, energy costs, by-product removal costs and the like.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount will range from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount of from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount of from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Examples of organic solvents include, but are not limited to, alcohols, in particular alkanols; glycols, in particular alkyl glycols; ketones; aldehydes; amines; tetrahydrofuran; nitrobenzene; nitrotoluene; glymes, in particular glyme, diglyme and tetraglyme; and the like. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range of from about 0.1% by weight up to the maximum solubility afforded by the particular solvent/solubilizing agent combination employed. It is generally very suitable to employ solutions containing from 0.5% to about 45% by weight of silver, with concentrations of from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e. a silver precursor, rhenium component, alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range of from about 200° C. to about 600° C., preferably from about 200° C. to about 500° C., and more preferably from about 200° C. to about 450° C., at a pressure in the range of from 0.5 to 35 bar. In general, the higher the temperature, the shorter the required heating period. A wide range of heating periods have been suggested in the art; e.g., U.S. Pat. No. 3,563,914 suggests heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Non-limiting examples include nitrogen, argon, krypton, helium, and combinations thereof, with the preferred inert gas being nitrogen. Non-limiting examples of the oxygen-containing oxidizing component include molecular oxygen ($O_2$), $CO_2$, NO, $NO_2$, $N_2O$, $N_2O_3$, $N_2O_4$, or $N_2O_5$, or a substance capable of forming NO, $NO_2$, $N_2O$, $N_2O_3$, $N_2O_4$, or $N_2O_5$ under the calcination conditions, or combinations thereof, and optionally comprising $SO_3$, $SO_2$, trimethyl phosphite or combinations thereof. Of these, molecular oxygen is a useful embodiment, and a combination of $O_2$ with NO or $NO_2$ is another useful embodiment. In a useful embodiment, the atmosphere comprises from about 10 ppm to about 1% by volume of an oxygen-containing oxidizing component. In another useful embodiment, the atmosphere comprises from about 50 ppm to about 500 ppm of an oxygen-containing oxidizing component.

In another embodiment, the impregnated support, which has been calcined as disclosed above, may optionally thereafter be contacted with an atmosphere comprising a combination of oxygen and steam, which atmosphere is substantially absent of an olefin, and preferably, completely absent of an olefin. The atmosphere usually comprises from about 2% to about 15% steam by volume, preferably from about 2% to about 10% steam by volume, and more preferably from about 2% to about 8% steam by volume. The atmosphere usually comprises from about 0.5% to about 30% oxygen by volume, preferably from about 1% to about 21% oxygen by volume, and more preferably from about 5% to about 21% oxygen by volume. The balance of the gas atmosphere may be comprised of an inert gas. Non-limiting examples of the inert gas include nitrogen, argon, krypton, helium, and combinations thereof, with the preferred inert gas being nitrogen. The contacting is usually conducted at a temperature of from about 200° C. or higher. In one embodiment the contacting is conducted at a temperature of from about 200° C. to about 350° C. In another embodiment the contacting is conducted at a temperature of from about 230° C. to about 300° C. In another embodiment the contacting is conducted at a temperature of from about 250° C. to about 280° C. In another embodiment the contacting is conducted at a temperature of from about 260° C. to about 280° C. Usually the contacting is conducted for from about 0.15 hour or more. In one embodiment the contacting is conducted for from about 0.5 hour to about 200 hours. In another embodiment the contacting is conducted for from about 3 hours to about 24 hours. In another embodiment the contacting is conducted for from about 5 hours to about 15 hours.

Ethylene Oxide Production

The epoxidation process may be carried out by continuously contacting an oxygen-containing gas with an olefin, which is preferably ethylene, in the presence of the catalyst produced by the invention. Oxygen may be supplied to the reaction in substantially pure molecular form or in a mixture such as air. Molecular oxygen employed as a reactant may be obtained from conventional sources. Reactant feed mixtures may contain from about 0.5% to about 45% ethylene and from about 3% to about 15% oxygen, with the balance comprising comparatively inert materials including such substances as carbon dioxide, water, inert gases, other hydrocarbons, and one or more reaction modifiers such as organic halides. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum. Non-limiting examples of reaction moderators include organic halides such as $C_1$ to $C_8$ halohydrocarbons. Preferably, the reaction moderator is methyl chloride, ethyl chloride, ethylene dichloride, ethylene dibromide, vinyl chloride or mixtures thereof. Most preferred reaction moderators are ethyl chloride and ethylene dichloride. Usually such reaction moderators are employed in an amount of from about 0.5 to 10 ppmv, preferably from 1 to 8 ppmv of the total volume of the feed gas.

A usual method for the ethylene epoxidation process comprises the vapor-phase oxidation of ethylene with molecular oxygen, in the presence of the inventive catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst. Typical operating conditions for the ethylene epoxidation process involve temperatures in the range of from about 180° C. to about 330° C., and preferably, about 200° C. to about 325° C., and more preferably from about 225° C. to about 270° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 0.1-5 seconds. The present catalysts are effective for this process when operated within these ranges of conditions.

The resulting ethylene oxide is separated and recovered from the reaction products using conventional methods. For this invention, the ethylene epoxidation process may include a gas recycle wherein substantially all of the reactor effluent is readmitted to the reactor inlet after substantially or partially removing the ethylene oxide product and the byproducts. In the recycle mode, carbon dioxide concentrations in the gas inlet to the reactor may be, for example, from about 0.3 to 6 volume percent.

The inventive catalysts have been shown to be particularly selective for oxidation of ethylene with molecular oxygen to ethylene oxide. The conditions for carrying out such an oxidation reaction in the presence of the catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity of 1500-10,000 h$^{-1}$, a reactor inlet pressure of 150-400 psig, a coolant temperature of 180-315° C., an oxygen conversion level of 10-60%, and an EO production rate (work rate) of 2-16 lbs. EO/cu. ft. catalyst/hr. The feed composition at the reactor inlet may typically comprises 1-40% ethylene, 3-12% $O_2$, 0.3-40% $CO_2$, 0-3% ethane, 0.3-20 ppmv total concentration of organic chloride moderator(s), and the balance of the feed being comprised of argon, methane, nitrogen or mixtures thereof.

The following non-limiting examples serve to illustrate the invention.

EXAMPLES

Aluminum Oxides

The following aluminas were used for the preparation of the catalysts. The different types of alumina supports are available from Saint-Gobain Norpro Co., Noritake Co., Sued Chemie AG and/or CeramTec AG.

|  | Support A | Support B | Support C |
|---|---|---|---|
| BET surface, m$^2$/g$^{(a)}$ | 0.6 | 0.8 | 1.0 |
| Water absorption, cc/g | 0.43 | 0.45 | 0.39 |
| Total pore volume, Hg, cc/g$^{(b)}$ | 0.37 | 0.44 | 0.39 |

$^{(a)}$Determined according to the Method of Brunauer, Emmet and Teller
$^{(b)}$Mercury intrusion data to 44.500 psia using Micrometrics AutoPore IV 9500 (140° contact angle, 0.480 N/m surface tension of mercury)

Catalyst Preparation
Silver Solution

An 834 g portion of high purity silver oxide (Ames Goldsmith Corp.) was added to a stirred solution of 442 g oxalic acid dehydrate (ACS Certified Reagent, Fisher) in about 2,800 g deionized water. A precipitate of hydrated silver oxalate salt formed on mixing. Stirring was continued for 0.5 hours. The precipitate was then collected on a filter and washed with deionized water. Analysis showed that the precipitate contained 50.5 wt % silver. Next, 213.9 g of the silver oxalate precipitate was dissolved in a mixture of 77.2 grams ethylenediamine (99+%, Aldrich) and 60.3 g deionized water. The temperature of the solution was kept below 40° C. by combining the reagents slowly, and by cooling the solution. After filtration, the solution contained roughly 30 wt % silver, and had a specific gravity of 1.52 g/mL.

Example 1

Catalyst A

A 150 g portion of alumina support A was placed in a flask and evacuated to ca. 0.1 torr prior to impregnation. To the above silver solution were added aqueous solutions of cesium hydroxide, perrhenic acid, and ammonium sulfate in order to prepare a catalyst composition according to examples 5-10 of U.S. Pat. No. 4,766,105. After thorough mixing, the promoted silver solution was aspirated into the evacuated flask to cover the carrier while maintaining the pressure at ca. 0.1 torr. The vacuum was released after about 5 minutes to restore ambient pressure, hastening complete penetration of the solution into the pores. Subsequently, the excess impregnation solution was drained from the impregnated carrier. Calcination of the wet catalyst was done on a moving belt calciner. In this unit, the wet catalyst is transported on a stainless steel belt through a multi-zone furnace. All zones of the furnace are continuously purged with pre-heated, ultra-high purity nitrogen and the temperature is increased gradually as the catalyst passes from one zone to the next. The heat is radiated from the furnace walls and from the preheated nitrogen.

In this Example 1, the wet catalyst entered the furnace at ambient temperature. The temperature was then increased gradually to a maximum of about 450° C. as the catalyst passed through the heated zones. In the last (cooling) zone, the temperature of the now activated was immediately lowered to less than 100° C. before it emerged into ambient atmosphere. The total residence time in the furnace was approximately 45 minutes. The bimodal pores size distribution of the alumina support A is illustrated in Table I.

Example 2

Catalyst B

Catalyst B was prepared with alumina support B following the procedure of Catalyst A. The bimodal pore size distribution of the alumina support B is illustrated in Table I.

Example 3

Catalyst C

Comparative Example

Catalyst C was prepared with alumina support C following the procedure of Example. The monomodal pore size distribution of the alumina support C is illustrated in Table I. In addition, three catalyst containing only silver and cesium were prepared with the same alumina.

Example 4

Catalyst D

A 150 g portion of alumina support A was placed in a flask and evacuated to ca. 0.1 torr prior to impregnation. To the above silver solution were added aqueous solutions of cesium hydroxide in order to prepare a catalyst with 14.1 wt % silver, similar to example 1 through 3, and 350 ppm cesium, based on the total weight of the catalyst. After thorough mixing, the cesium-promoted silver solution was aspirated into the evacuated flask to cover the carrier while maintaining the pressure at ca. 0.1 torr. The vacuum was released after about 5 minutes to restore ambient pressure, hastening complete penetration of the solution into the pores. Subsequently, the excess impregnation solution was drained from the impregnated carrier. Calcination of the wet catalyst was done on a moving belt calciner. In this unit, the wet catalyst is transported on a stainless steel belt through a multi-zone furnace. All zones of the furnace are continuously purged with pre-heated, ultra-high purity nitrogen and the temperature is increased gradually as the catalyst passes from one zone to the next. The heat is radiated from the furnace walls and from the preheated nitrogen. In this Example 4, the wet catalyst entered the furnace at ambient temperature. The temperature was then increased gradually to a maximum of about 450° C. as the catalyst passed through the heated zones. In the last (cooling) zone, the temperature of the now activated was immediately lowered to less than 100° C. before it emerged into ambient atmosphere. The total residence time in the furnace was approximately 45 minutes.

Example 5

Catalyst E

Catalyst E was prepared with alumina support B following the procedure of Catalyst D.

Example 6

Catalyst F

Catalyst F was prepared with alumina support C following the procedure of Catalyst D, except that the cesium target was 400 ppm based on the total weight of the catalyst.

Testing of the Catalyst

For testing, the catalyst was charged into a fixed-bed stainless steel tube reactor (¼ inch approximate inner diameter), which was embedded in a heated copper block. The catalyst charge consisted of 4 g crushed catalyst (1.0-1.4 mm particle size) mixed with 8.6 grams of inert material and the inlet gas flow was adjusted to give a gas hour space velocity of 12375 $h^{-1}$ and 0.83 Nl/min respectively. The feed gas composition by volume was 15% ethylene, 7% oxygen, 5% carbon dioxide, 1.7 ppmv ethyl chloride, and nitrogen balance. Reaction pressure was maintained at 19.4 atm. The reactor effluent was analyzed by mass spectrometry at roughly 1-hour intervals. In the case of Examples 1 through 3, the temperature was adjusted to maintain 2.0% EO in the reactor outlet for a productivity of 486 g-EO per kg-catalyst per hour. The catalyst was kept under these conditions until the maximum selectivity was observed. The result is listed, hereinafter, in Table II. In the case of Example 4 through 6, the temperature was adjusted to maintain 1.5% EO in the reactor outlet for a productivity of 356 g-EO per kg-catalyst per hour. The catalyst was kept under these conditions until the maximum selectivity was observed. The result is listed, hereinafter, in Table III.

TABLE I

Pore size distribution of used carrier

| | | | Mode 1 | | Mode 2 | |
|---|---|---|---|---|---|---|
| Example | Total pore volume[a] [cc/g] | Surface area[b] [m²/g] | Mean Pore Diameter [μm] | Pore volume [%]* | Mean Pore Diameter [μm] | Pore volume [%]* |
| 1 | 0.37 | 0.6 | 0.7 | 25 | 15.8 | 69 |
| 2 | 0.44 | 0.7 | 1.3 | 60.0 | 18.5 | 37 |
| 3 | 0.39 | 1.0 | monomodal distribution, pores ≦7 provide 90% Avg. diameter | | | |

[a]Mercury intrusion data to 44.500 psia using Micrometrics AutoPore IV 9500 (140° contact angle, 0.480 N/m surface tension of mercury)
[b]Determined according to the Method of Brunauer, Emmet and Teller
*Percentage of the total pore volume of the catalyst
Pores larger than the second mode provide the remaining pore volume up to 100%.

TABLE II

Test results with rhenium containing catalysts

| Example | Selectivity [% mole] | Temperature [° C.] |
|---|---|---|
| 1 | 87.6 | 254 |
| 2 | 87.6 | 257 |
| 3 | 86.5 | 258 |

TABLE III

Test results with catalyst containing silver and cesium only

| Example | Selectivity [% mole] | Temperature [° C.] |
|---|---|---|
| 4 | 82.0 | 239 |
| 5 | 82.3 | 239 |
| 6 | 82.6 | 224 |

Porosities are determined by the mercury porosimeter method; see Drake and Ritter, "Ind. Eng. Chem. anal. Ed.," 17, 787 (1945). Pore and pore diameter distributions are determined from the surface area and apparent porosity measurements. BET method: See J. Am. Chem. Soc. 60, 3098-16 (1938)

While the present invention has been demonstrated and described with reference to preferred embodiments, it will be readily appreciated by those of ordinary skill in the art that various changes and modifications may be made without departing from the spirit and scope of the invention. It is therefore intended that the claims be interpreted to cover the disclosed embodiment, those alternatives which have been discussed, and any and all equivalents thereto.

What is claimed is:

1. A catalyst for the epoxidation of an olefin to an olefin oxide comprising a support having a bimodal pore size distribution, with a first mode of pores which has a mean diameter ranging from about 0.01 μm to about 5 μm, and a second mode of pores which has a mean diameter ranging from about 5 μm to about 30 μm; a catalytically effective amount of silver or a silver-containing compound effective for the epoxidation of an olefin to an olefin oxide, a promoting amount of rhenium or a rhenium-containing compound, and a promoting amount of one or more alkali metals or alkali-metal-containing compounds.

2. The catalyst of claim 1 wherein the first mode of pores has a mean diameter ranging from about 0.1 μm to about 4 μm and the second mode of pores has a mean diameter ranging from about 5 μm to about 20 μm.

3. The catalyst of claim 1 wherein the first mode of pores comprises at most 50% of a total pore volume and the second mode of pores comprises at least 50% of the total pore volume.

4. The catalyst of claim 1 wherein the first mode of pores comprises at most 40% of a total pore volume and the second mode of pores comprises at least 60% of the total pore volume.

5. The catalyst of claim 1 wherein the support comprises alumina, charcoal, pumice, zirconia, titania, kieselguhr, fuller's earth, silicon carbide, silica, magnesia, clays, artificial zeolites, natural zeolites, ceramics, or a combination thereof.

6. The catalyst of claim 1 wherein the support comprises alumina.

7. The catalyst of claim 1 wherein the support comprises alumina having a surface area of less than about 1 m²/g.

8. The catalyst of claim 1 further comprising a promoting amount of one or more Group IIA metal-containing compounds, one or more transition metal-containing compounds, one or more sulfur-containing compounds, one or more fluorine-containing compounds, one or more phosphorus-containing compounds, one or more boron-containing compounds, or a combination thereof.

9. The catalyst of claim 8 wherein the Group IIA metal-containing compound comprises beryllium, magnesium, calcium, strontium, barium or a combination thereof.

10. The catalyst of claim 8 wherein the transition metal-containing compound comprises an element selected from Groups IVA, VA, VIA, VIIA and VIIIA of the Periodic Table of the Elements, or a combination thereof.

11. The catalyst of claim 8 wherein the transition metal-containing compound comprises molybdenum, tungsten, chromium, titanium, hafnium, zirconium, vanadium, thorium, tantalum, niobium or a combination thereof.

12. The catalyst of claim 8 wherein the transition metal-containing compound comprises molybdenum, tungsten, or a combination thereof.

13. The catalyst of claim 1 wherein the catalyst further comprises a promoting amount of gallium, germanium, sulfur, phosphorus, boron, a halogen, or a combination thereof, on the surface of the support.

14. The catalyst of claim 1 wherein the alkali metal-containing compound comprises lithium, sodium, potassium, rubidium, cesium or a combination thereof.

15. The catalyst of claim 1 wherein the alkali metal-containing compound comprises cesium.

16. The catalyst of claim 1, wherein said support has a surface acidity less than 2 micromoles per gram of support, as determined by irreversible ammonia sorption at 100° C.

17. The catalyst of claim 1, wherein said support has a surface acidity less than 1.5 micromoles per gram of support, as determined by irreversible ammonia sorption at 100° C.

* * * * *